United States Patent [19]

Ayer et al.

[11] Patent Number: 5,035,897
[45] Date of Patent: Jul. 30, 1991

[54] DOSAGE FORM FOR DELIVERING SOLUBLE OR INSOLUBLE DRUGS

[75] Inventors: Atul D. Ayer; Anthony L. Kuczynski; Patrick S. Wong, all of Palo Alto, Calif.

[73] Assignee: Alza Corporation, Palo Alto, Calif.

[21] Appl. No.: 403,523

[22] Filed: Sep. 5, 1989

[51] Int. Cl.$^5$ .................................................. A61K 9/24
[52] U.S. Cl. ..................................... 424/473; 424/472
[58] Field of Search ........................ 424/473, 469, 470

[56] References Cited

U.S. PATENT DOCUMENTS

| | | | |
|---|---|---|---|
| 2,798,053 | 6/1957 | Brown | 260/2.2 |
| 2,799,241 | 6/1957 | Wurster | 118/24 |
| 2,909,462 | 10/1959 | Warfield et al. | 167/56 |
| 3,133,132 | 5/1964 | Loeb et al. | 264/49 |
| 3,173,876 | 3/1965 | Zobrist | 252/137 |
| 3,276,586 | 10/1966 | Rosaen | 210/90 |
| 3,541,005 | 11/1970 | Strathmann et al. | 210/19 |
| 3,541,006 | 11/1970 | Bixler et al. | 210/23 |
| 3,546,142 | 12/1970 | Michaels et al. | 260/2.1 |
| 3,845,770 | 11/1974 | Theeuwes et al. | 128/260 |
| 3,865,108 | 2/1975 | Hartop | 128/260 |
| 3,916,899 | 11/1975 | Theeuwes et al. | 128/260 |
| 4,002,173 | 1/1977 | Manning et al. | 128/296 |
| 4,063,064 | 12/1977 | Saunders et al. | 219/121 L |
| 4,088,864 | 5/1978 | Theeuwes et al. | 219/121 LM |
| 4,160,020 | 7/1979 | Ayer et al. | 424/15 |
| 4,200,098 | 4/1980 | Ayer et al. | 128/260 |
| 4,207,893 | 6/1980 | Michaels | 128/260 |
| 4,285,987 | 8/1981 | Ayer et al. | 427/3 |
| 4,309,996 | 2/1982 | Theeuwes | 128/260 |
| 4,320,759 | 3/1982 | Theeuwes | 128/260 |
| 4,327,725 | 5/1982 | Cortese et al. | 128/260 |
| 4,765,989 | 8/1988 | Wong et al. | 424/473 |

OTHER PUBLICATIONS

Remington's *Pharmaceutical Sciences*, 14th Ed. (1970), p. 247.
*Encyclopaedic Dictionary of Physics*, vol. 6 (1962), pp. 547–557.
*J. Am. Phar. Assoc.*, Sci. Ed., vol. 48 (1959), pp. 451–459.
*J. Am. Phar. Assoc.*, Sci. Ed., vol. 49 (1960), pp. 82–84.

*Primary Examiner*—Merrell C. Cashion, Jr.
*Assistant Examiner*—Leon C. Horne
*Attorney, Agent, or Firm*—Paul L. Sabatine; Edward L. Mandell; Steven F. Stone

[57] ABSTRACT

A dosage form is disclosed comprising granule means for delivering soluble to insoluble drug to a warm-blooded animal.

6 Claims, 2 Drawing Sheets

DOSAGE FORM FOR DELIVERING SOLUBLE OR INSOLUBLE DRUGS

DESCRIPTION OF TECHNICAL FIELD

This invention concerns a dosage form for delivering a soluble or an insoluble drug. More particularly, the invention pertains to a dosage form comprising (1) a wall that surrounds, (2) a compartment, (3) granules in the compartment comprising an aqueous soluble or insoluble drug, (4) means in the compartment for displacing the drug from the compartment, and (5) exit means in the wall that connects the exterior with the interior of the dosage form for delivering the drug in a controlled pattern to a drug receiving environment over time.

DESCRIPTION OF BACKGROUND ART

A critical need exists for a dosage form for delivering an aqueous soluble or an aqueous insoluble drug orally to a patient in one or two doses per day to assure constant availability of drug. The need exists for a dosage form for delivering an aqueous soluble drug because (1) aqueous soluble drugs are difficult to formulate into a dosage form, such as an osmotic dosage form, and because (2) aqueous soluble drugs often are prematurely released from the dosage form by unwanted diffusion, or by interaction with a fluid in a gastrointestinal environment, thereby extracting the drug from the dosage form. The need exists for a dosage form for delivering an aqueous insoluble drug because (3) aqueous insoluble drugs are difficult to delivery from a dosage form, such as an osmotic dosage form, as these drugs lack the kinetic ability to develop an osmotic pressure gradient, and because (4) aqueous insoluble drugs are delivered as intact solid forms and they may cause irritation of the mucosa of the gastrointestinal tract.

In the light of the above presentation it will be appreciated by those versed in the dispensing arts to which this invention pertains that a critical need exists for, (5) a dosage form that can deliver both soluble and insoluble aqueous drugs at a controlled rate to provide a dosage, therapeutic administration of drug in either instance for its beneficial effects over a prolonged time span, and for (6) a dosage form that can administer a drug essentially independent of its chemical properties. It will be further appreciated by those versed in the medical art that a novel and unique dosage form that can administer such a drug at a controlled rate over time, and simultaneously provide substantial therapy, would represent an advancement and a valuable contribution to the art.

DESCRIPTION OF OBJECTS OF THE INVENTION

Accordingly, in view of the above presentation, it is an immediate object of this invention to provide a dosage form for delivering soluble and insoluble drugs at a controlled rate, and which dosage form substantially overcomes the disadvantages associated with the prior art.

Another object of the invention is to provide a dosage form comprising granules comprising a drug that can be delivered at a controlled rate by the dosage form over time.

Another object of the invention is to provide a dosage form manufactured as an osmotic device, which comprises granules comprising an aqueous soluble or aqueous insoluble drug that is delivered in a uniform release pattern by the dosage form over time.

Another object of the present invention is to provide a dosage form comprising drug granules, which granules comprise a therapeutic drug core and a granule forming component.

Another object of the invention is to provide a dosage form comprising granules of drug comprising a pharmaceutically acceptable coating that surrounds a therapeutic drug core.

Another object of the invention is to provide a dosage form manufactured as an osmotic dosage form comprising a multiplicity of small discrete granule units that can be delivered as multiple unit dosage forms to effect controlled drug delivery over time.

Another object of the invention is to provide a dosage form manufactured as an osmotic device comprising a multiplicity of granules pressed into an initial layer for release as individual dosage units from the osmotic device over time.

Another object of the invention is to provide a dosage form comprising granules of drug to provide a predetermined dose or a number of doses of drug over time which drug is designed to produce a therapeutic effect.

Another object of the invention is to provide an osmotic dosage form comprising granules that releases the pharmaceutical drug therein to a warm-blooded animal at a controlled rate and in a dosage amount available at a relatively constant level over an extended period of time.

Another object of the invention is to provide an osmotic dosage form comprising therapeutic granules, which dosage form and granules act together to effect an improvement in drug delivery over time.

Other objects, features and advantages of the invention will be more apparent to those skilled in the art from the following detailed specification, taken in conjunction with the drawing figures and the accompanying claims.

BRIEF DESCRIPTION OF THE INVENTION DRAWINGS

In the drawing figures, which are not drawn to scale, but are set forth to illustrate various embodiments of the invention, the drawing figures are as follows.

In the drawings and in the specification, like parts in related figures are identified by like numbers. The terms appearing earlier in the specification and in the descrip-

3 tion of the drawings, as well as embodiments thereof, are further detailed elsewhere in the disclosure.

DETAILED DISCLOSURE OF INVENTION DRAWINGS

Figure 1:
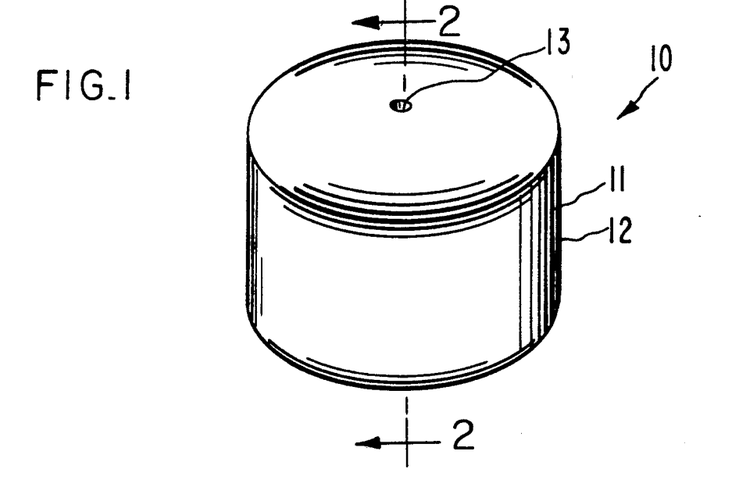
FIG. 1 is a view of the dosage form manufactured as an osmotic device designed for orally administering a beneficial drug to the gastrointestinal environment of a warm-blooded animal.

Turning now to the drawing figures in detail, which drawings are examples of various dosage forms provided by the invention, and which examples are not to be construed as limiting, one embodiment of dosage form manufactured as an osmotic device is seen in FIG. 1 as indicated by the numeral 10. In FIG. 1, dosage form 10 is manufactured as an oral osmotic device comprising a body 11 that can be shaped, sized, adapted and structured for easy placement and prolonged retention in a biological environment of use for controlled delivery of a beneficial agent thereto. Osmotic dosage form 10 comprises a wall 12 with at least one passageway 13 through wall 12 for connecting the inside of the dosage form with the exterior of dosage form.

Figure 2:
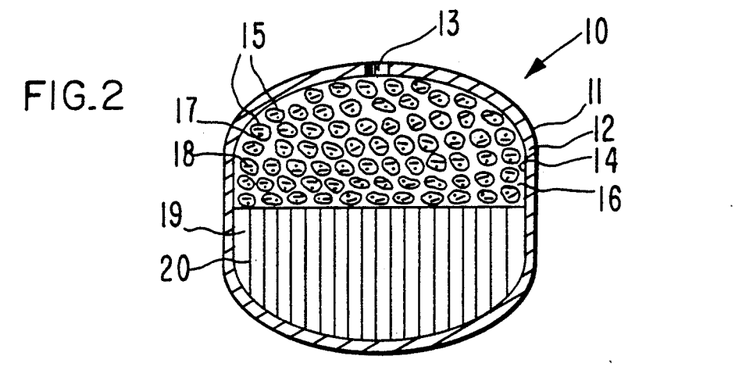
FIG. 2 is an opened view of FIG. 1 through 2—2 illustrating the structure of the dosage form comprising granules of drug in the dosage form.

In FIG. 2, osmotic device 10 is seen in opened-section. In FIG. 2, device 10 comprises a body 11 comprising wall 12 that surrounds and defines an internal compartment 14. Wall 12 comprises, in one embodiment, a semipermeable polymeric composition that is permeable to the passage of an exterior fluid and substantially impermeable to the passage of drugs and other agents present in compartment 14. Wall 12, in another embodiment, comprises in at least a part a semipermeable polymeric composition with the remaining part comprising a nonsemipermeable polymeric composition, which latter composition is impermeable to the passage of fluid, drug, and other agents optionally present in compartment 14. Wall 12 of device 10 is substantially inert, it maintains its physical and chemical integrity during the dispensing of an active beneficial drug, and it comprises materials nontoxic to a host. A passageway 13 in wall 12 connects compartment 14 with the exterior of device 10. Compartment 14 houses a plurality of granules 15. The granules 15 are present in compartment 14 as a first lamina 16, which can also be defined optionally as a first composition 16. The granules 15 comprise a homogenous blend of a drug 17 and granule forming ingredients 18. In a presently preferred embodiment, the granule forming ingredients exhibit an osmotic pressure gradient across wall 12 against an external fluid, and in this embodiment they cooperate with device 10 for delivering drug 17 to an environment of use through passageway 13 over time.

Compartment 14 comprises also a second lamina 19. First lamina 16 and a second lamina 19 initially are in laminar arrangement, and they cooperate with each other and with dosage form 10 for the effective delivery of drug 17 from dosage form 10. The second lamina 19 comprises an expandable driving member 20 comprising a hydrogel that imbibes and absorbs water thereby expanding and displacing the granules 15 from dosage form 10. The presently preferred hydrogel is a hydrophilic polymer, which possesses osmotic properties such as the ability to imbibe an external fluid and exhibit an osmotic pressure across wall 12.

Figure 3:
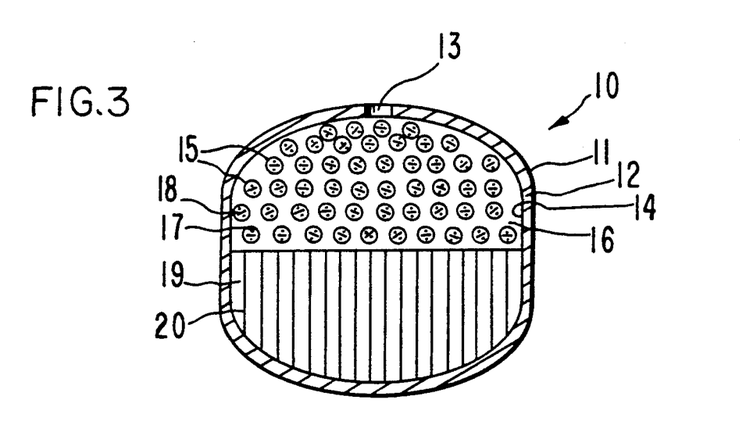
FIG. 3 is an opened view of the dosage form of FIG. 1 depicting the dosage form comprising granules comprising drug in another embodiment present in the dosage form.

In FIG. 3, another dosage form 10 provided by the invention, is seen in opened-section. In FIG. 3, dosage form 10 comprises body 11, wall 12, passageway 13, compartment 14, first lamina 16 comprising granules 15, which granules comprise drug 17 and granule forming ingredient 18; and second lamina 19 comprising expandable, displacement member 20. The granules in this manufacture comprise a granule forming wall 15 that surrounds drug 17 and granule forming ingredient 18.

Figure 4:
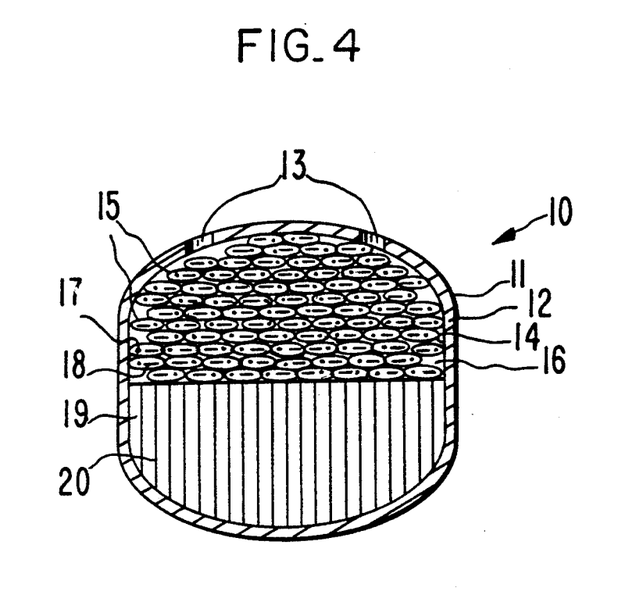
FIG. 4 is an opened view of the dosage form of FIG. 1 illustrating the dosage form comprising granules in compressed arrangement in the dosage form; and, FIG. 5 is a graph that sets forth the molecular weight of polyvinylpyrrolidone in relation to its viscosity and degree of polymerization.

Drawing FIG. 4 depicts another manufacture of dosage form 10 provided by the invention. In this manufacture, dosage form 10 comprises body 11, wall 12, a plurality of passageways 13, compartment 14, a first lamina 16, which lamina 16 comprises a multiplicity of compressed granules, said granules comprising drug 17 and a granule forming member 17. The dosage form also comprises a second lamina 19 comprising a hydrogel member 20. The granules in this manufacture are compressed into a layer for bilayering with the expandable hydrogel to improve the manufacture of dosage form 10.

FIGS. 1 through 4 are illustrative of various dosage forms that can be made according to the invention, and it is to be understood these dosage forms are not to be construed as limiting, as the dosage form can take a wide variety of shapes, sizes and forms adapted for delivering a drug to various environments of use. For example, the dosage forms include buccal, implant, topical, nose, artificial gland, rectum, cervical, intrauterine, vaginal, ear, and the like.

DISCLOSURE OF MODES OF THE INVENTION

In accordance with this invention, dosage form 10 comprises a wall 12, which wall comprises a composition that does not adversely affect the granule, granule forming ingredients, the drug, the expandable member, other ingredients optionally housed in dosage form 10, and a warm-blooded animal. Wall 12 is permeable in at least a part, to the passage of an external fluid such as water and biological fluids, and it is substantially impermeable to the passage of drug, hydrogel, and the like. In a preferred embodiment, the wall is nonerodible and insoluble in fluid during the drug delivery period.

In one embodiment, representative materials for forming a semipermeable wall comprise a cellulose ester, a cellulose ether, and cellulose ester-ethers. These cellulosic polymers have a degree of substitution, D.S., on the anhydroglucose unit, from greater than 0 up to 3, inclusive. By degree of substitution is meant the average number of hydrogel groups originally present on the anhydroglucose unit comprising the cellulose polymer that are replaced by substituting groups. Representative compositions include a member selected from the group consisting of cellulose acylate, cellulose diacylate, cellulose triacylate, cellulose acetate, cellulose diacetate, cellulose triacetate, monocellulose alkanylates, dicellulose alkanylates, tricellulose alkanylates, monocellulose aroylates, dicellulose aroylates, tricellulose aroylates, and the like. Exemplary polymers include cellulose acetate having a D.S. up to 1 and an acetyl content up to 21%; cellulose acetate having an acetyl content of 32% to 39.8%; cellulose acetate having a D.S. of 1 to 2 and an acetyl content of 21% to 35%; cellulose acetate having a D.S. of 2 to 3 and an acetyl content of 35% to 44.8%; and the like. More specific cellulose polymers comprise cellulose propionate having a D.S. of 1.8, a propyl content of 39.2% to 45% and a hydroxyl content of 2.8% to 5.4%; cellulose acetate butyrate having a D.S. of 1.8, an acetyl content of 13 to 15 and a butyryl content of 34% to 39%; cellulose acetate butyrate having an acetyl content of 2% to 29%, a butyryl content of 17% to 53% and a hydroxyl content of 0.5% to 4.7%; cellulose triacylates having a D.S. of 2.9 to 3 such as cellulose trivalerate, cellulose trilaurate, cellulose tripalmitate, cellulose trisuccinate and cellulose trioctanoate; cellulose diacylates possessing a D.S. of 2.2 to 2.6 such as cellulose disuccinate, cellulose dipalmitate, cellulose dioctanoate, and cellulose dipentanoate; coesters of cellulose such as cellulose acetate butyrate and cellulose acetate propionate, and the like.

Additional wall forming polymers comprise ethyl cellulose comprising a degree of etherification with an ethoxy content of 40 to 55%; acetaldehyde dimethylcellulose acetate; cellulose acetate ethylcarbamate; cellulose acetate methylcarbamate; cellulose acetate dimethylaminoacetate; semipermeable polyamides; semipermeable polyurethanes; semipermeable sulfonated polystyrenes; semipermeable cross-linked selected polymers formed by the coprecipitation of a polyanion and a polycation as disclosed in U.S. Pat. Nos. 3,173,876; 3,276,586; 3,541,005; 3,541,006, and 3,546,142; semipermeable polymers as disclosed by Loeb and Sourirajan in U.S. Pat. No. 3,133,132; semipermeable lightly cross-linked polystyrene derivatives; semipermeable cross-linked poly(vinylbenzyltrimethyl ammonium) chloride; semipermeable polymers exhibiting a fluid permeability of $2.5 \times 10^{-11}$ to $2.5 \times 10^{-4}$ (cm$^2$/hr . atm), expressed per atmosphere of hydrostatic imbibition, or osmotic pressure difference across the semipermeable walls. The polymers are known to the art in U.S. Pat. Nos. 3,845,770; 3,916,899; and 4,160,020; and in *Handbook of Common Polymers*, by Scott, J.R., and Roff, W.J., (1971) published by CRC Press, Cleveland, Ohio.

Figure 5:
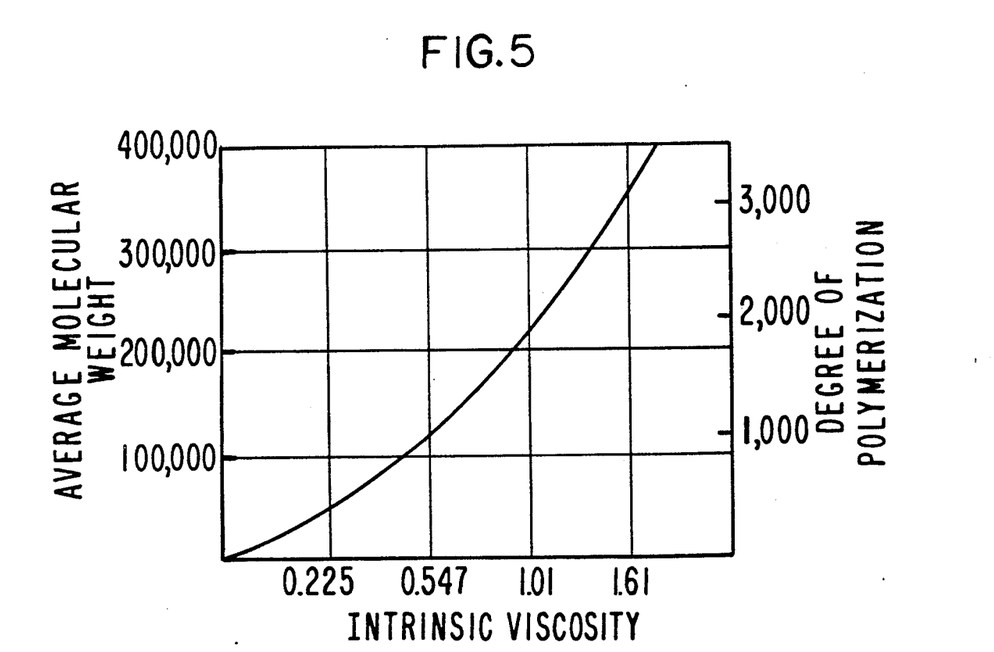

Granules 15 in compartment 14 comprise, in one preferred manufacture, a film that surrounds a drug and a granule-forming binder. The film comprises, in a presently preferred embodiment a polyvinylpyrrolidone comprising a molecular weight of about 10,000 to 500,000 and a K-value of 10 to 150. The expression, "K-value," for polyvinylpyrrolidone, represents a function of the average molecular weight. K-values are derived from viscosity measurements and they are calculated according to Fikentscher'formula as follows:

$$\frac{\log \eta \text{ rel}}{C} = \frac{75 K_o^2}{1 + 1.5_{oc}} + K_o$$

wherein c equals concentration in g/100 ml solution; $\eta$ rel equals viscosity of the solution compared with solvent, and K equals 1,000$K_o$, as seen in accompanying FIG. 5, which depicts the relation of molecular weight, degree of polymerization and intrinsic viscosity of polyvinylpyrrolidone. Representative of polyvinylpyrrolidone comprises a polyvinylpyrrolidone comprising a 10,000 molecular weight and a K-value of 15-21, a polyvinylpyrrolidone comprising a 40,000 molecular weight and a K-value of 40,000, a polyvinylpyrrolidone comprising a 160,000 molecular weight and a K-value of 50-62, a polyvinylpyrrolidone comprising a 360,000 molecular weight and a K-value of 80-1,000, a polyvinylpyrrolidone comprising a 420,000 molecular weight and a K-value of 140-180, and the like. The granule forming film in another embodiment comprises copolymers of polyvinylpyrrolidone represented by copolymer polyvinylpyrrolidone with vinyl acetate, copolymer of polyvinylpyrrolidone and vinyl alcohol, copolymer of polyvinylpyrrolidone and vinyl chloride, copolymer of polyvinylpyrrolidone and vinyl fluoride, copolymer of polyvinylpyrrolidone and vinyl butyrate, copolymer of polyvinylpyrrolidone and vinyl laurate, copolymer of polyvinylpyrrolidone and vinyl stearate, and the like.

Granule 15 in compartment 14, comprises a binder mixed with the drug. The binder presently preferred comprises a hydroxyalkylcellulose ether. The hydroxyalkylcellulose ether comprises repeating units on the cellulose molecule containing one primary and two secondary groups that are substituted with ether groups, which ether groups comprise an alkyl moiety of 1 to 7 carbons. Representative hydroxyalkylcellulose ethers comprise hydroxymethylcellulose ether, hydroxyethylcellulose ether, hydroxypropylcellulose ether, hydroxybutylcellulose ether, hydroxypentylcellulose ether, hydroxytertpentylcellulose ether, hydroxyhexylcellulose ether, hydroxyisohexylcellulose ether, and the like. The hydroxyalkylcellulose ethers comprises an average molecular weight of 10,000 to 1,000,000. The granule comprises about 0.01 weight percent (wt %) to 75 wt % hydroxyalkylcellulose ether and about 0.01 wt % to 80 wt % of drug with the concentration of all ingredients surrounded by the film equal to 100 wt %. Granule 15, in the embodiment comprising a homogenous or heterogenous blend comprises 0.01 wt % to 50 wt % of polyvinylpyrrolidone and its copolymeric derivatives, about 0.01 wt % to 40 wt % of a hydroxyalkylcellulose ether, and about 0.01 wt % to 80 wt % of drug, with all components equal to 100 wt %. The dosage form, comprising the granules comprising 0.01 wt % to 80 wt %, generally delivers, in either instance, about 0.05 mg to 5 g, such as 1 mg, 5 mg, 10 mg, 25 mg, 100 mg, 125 mg, 250 mg, 750 mg, 1.0 g, 1.2 g, 1.5 g, and the like, over a prolonged period up to 24 hours.

The expressions, "soluble drug and insoluble drugs," as used herein, denotes the amount of drug, a solute, that dissolves in an aqueous solution, a solvent. A conventional pharmacopeial text, is disclosed in *Pharmaceutical Sciences*, by Remington, p 247 (1970) published by the Mack Publishing Company, Easton, Pa. The degree of solubility to insolubility of a drug is expressed in the accompanying table.

| SOLUBILITY TABLE | |
|---|---|
| SOLUBILITY | PARTS OF AQUEOUS SOLVENT FOR 1 PART OF DRUG SOLUTE |
| Very soluble | Less than 1 |
| Freely soluble | From 1 to 10 |
| Soluble | From 10 to 30 |
| Sparingly soluble | From 30 to 100 |
| Slightly soluble | From 100 to 1000 |
| Very slightly soluble | From 1000 to 10,000 |
| Practically insoluble | More than 10,000 |
| Insoluble | More than 10,000 |

Dosage form 10 comprises a drug that comprises any physiologically or pharmacologically active substance that produces a local or systemic effect in animals, including warm-blooded mammals, humans and primates; avians; household, sport and farm animals; laboratory animals; fishes; reptiles; and zoo animals. The term, "physiologically", as used herein, denotes the administration of a drug to produce generally normal levels and functions in a warm-blooded animal. The term, "pharmacologically" generally denotes variations in response to the amount of drug administered to the host. See *Stedman's Medical Dictionary*, (1966) published by Williams and Wilkins, Baltimore, Md.

The beneficial drug that can be delivered by the dosage form includes inorganic and organic compounds without limitation, including drugs that act on the peripheral nerve, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, organ systems, reproductive system, skeletal system, autacoid systems, alimentary and excretory systems, inhibitors of autacoids, and histamine systems. The therapeutic drug that can be delivered for acting on these recipients include anticonvulsants, analgesics, anti-Parkinsons, anti-inflammatories, anesthetics, antimicrobials, antimalarials, antiparasitic, antihypertensives, angiotensin converting enzyme inhibitor, antihistamines, antipyretics, alpha-adrenergic agonist, alpha-blockers, biocides, bactericides, bronchial dilators, beta-adrenergic stimulators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins, calcium channel blockers, and the like.

Drugs that can be delivered by dosage form 10 are drugs that are very soluble in aqueous fluids such as prochlorperazine edisylate, ferrous sulfate, aminocaproic acid, potassium chloride, mecamylamine hydrochloride, procainamide hydrochloride, amphetamine sulfate, benzphetamine hydrochloride, isoproterenol sulfate, methamphetamine hydrochloride, phenmetrazine hydrochloride, bethanechol chloride, methacholine chloride, methacholine chloride, pilocarpine hydrochloride, atropine sulfate, scopolamine bromide, isopropamide iodine, tridihexethyl chloride, phenformin hydrochloride, methylphenidate hydrochloride, cimetidine hydrochloride theophylline cholinate, cephalexin hydrochloride, and the like.

Exemplary drugs that can be delivered by dosage form 10 and are slightly soluble in aqueous fluid comprise diphenidol, meclizine hydrochloride, prochlorperazinemaleate, phenoxybenzamine, thiethylperazine maleate, anisindone, diphenadione, erythritol tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, estrogenic, progestational, corticosteroids, hydrocortisone, hydrocorticosterone acetate, cortisone acetate, triamcinolone, methyltesterone, 17-beta-estradiol, ethinyl estradiol, prazosin hydrochloride, ethinyl estradiol 3-methyl ether, prednisolone, 17-alpha-hydrocyprogesterone acetate, 19-norprogesterone, norgestrel, norethindrone, progesterone, norgesterone, norethynodrel, and the like.

Examples of other drugs that can be delivered by dosage form 10 comprise aspirin, indomethacin, naproxen, fenoprofen, sulindac, indoprofen, nitroglycerin, propranolol, timolol, atenolol, alprenolol, cimetidine, clonidine, imipramine, levodopa, chlorpromazine, methyldopa, dihydroxyphenylalanine, pivaloyloxyethyl ester of alpha methyldopa, theophylline, calcium gluconate, ketoprofen, ibuprofen, cephalexin, erythromycin, haloperidol, zomepirac, ferrous lactate, vincamine, diazepam, captopril, phenoxybenzamine, nifedipine, diltiazem, verapamil, milrinone, madol, quanbenz, hydrochlorothiazide, and the like. The beneficial drugs are known to the art in *Pharmaceutical Sciences*, 14th Ed., edited by Remington, (1979) published by Mack Publishing Co., Easton, Pa.; *The Drug, The Nurse, The Patient, Including Current Drug Handbook*, by Falconer et al., (1974–1976) published by Sunder Co., Philadelphia, Pa.; *Medicinal Chemistry*, 3rd Ed., Vol. 1 and 2, by Burger, published by Wiley-Interscience, NY and in *Physicians' Desk Reference*, 43th Ed., (1989) published by Medical Economics Co., Oradell, N.J.

The drug in dosage form 10 can be in various forms, such as uncharged molecules, molecular complexes, pharmacologically acceptable salts such as hydrochloride, hydrobromide sulfate, laurate, palmitate, phosphate, nitrite, borate, acetate, maleate, tartrate, oleate, and salicylate. For acidic drugs, salts of metals, amines or organic cations; for example, quaternary ammonium can be used. Derivatives of drugs such as ester, ethers and amides can be used. Also, a drug that is water insoluble can be used in a form that is a water soluble derivative thereof to serve as a solute, and on its release from the device is converted by enzymes, hydrolyzed by body pH or other metabolic processes to the original biologically active form.

The solubility of a beneficial drug can be determined by known techniques. One method for ascertaining the solubility of an agent consists of preparing a saturated solution comprising the fluid plus the agent as ascertained by analyzing the amount of agent present in a definite quantity of the fluid. A simple apparatus for this purpose consists of a test tube of medium size fastened upright in a water bath maintained at a constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed; if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygienic Laboratory; *Encyclopedia of Science and Technology*, Vol. 12, pp 542–556, (1971) published by McGraw-Hill, Inc.; and *Encyclopaedic Dictionary of Physics*, Vol. 6, pp 547–557, (1962) published by Pergamon Press, Inc.

The expression, "exit means," as used herein, comprises means and methods suitable for the controlled metered release of drug from compartment 14 of dosage form 10. The exit means comprises at least one passageway, or the like, through wall 12 for communicating with compartment 14. The expression, "at least one passageway," comprises aperture, orifice, bore, pore, porous element, hollow fiber, capillary tube, porous overlay, porous insert, and the like. The expression also comprises a material that erodes or is leached from the wall in a fluid environment of use to produce at least one passageway in the wall. Representative materials suitable for forming at least one passageway, or a multiplicity of passageways, comprise erodible polymers such polyglycolic acid or a polylactic acid member in the wall, a gelatinous filament, polyvinyl alcohol, leachable materials such as fluid removable pore-forming polysaccharides, salts, oxides or the like. A plurality of passageways can be formed by leaching a material such as sorbitol, lactose, or the like from the wall. The passageway can have any shape such as round, triangular, square, elliptical, and the like. Dosage form 10 can be constructed with one or more passageways in spaced apart relations, or more than one passageway in spaced apart relations, or more than one passageway on a single surface of dosage form 10. Passageways and equipment for forming passageways are disclosed in Theeuwes et al U.S. Pat. Nos. 3,845,770 issued November, 1974; Theeuwes et al U.S. Pat. No. 3,916,899 issued November, 1975; Saunders et al U.S. Pat. No. 4,063,064 issued December, 1977; and Theeuwes et al. U.S. Pat. No. 4,088,864 issued May, 1978. Passageways in osmotic systems formed by leaching are disclosed in Ayer et al U.S. Pat. Nos. 4,200,098 issued April, 1980; Ayer et al U.S. Pat. No. 4,285,987 issued August, 1981; Theeuwes U.S. Pat. No. 4,309,996 issued January, 1982; and Theeuwes U.S. Pat. No. 4,320,759 issued March, 1982.

Representative of members 20 for consuming space that displaces drug from dosage form 10 through exit means 13 are at osmopolymers also known as hydrogels. The hydrogel in the dispenser comprises a shape that corresponds to the internal shape of lumen 14. The hydrogel composition is noncross-linked or, optionally, cross-linked and it possesses osmotic properties such as the ability to imbibe an exterior fluid through semipermeable wall 12 and exhibits an osmotic pressure gradient across semipermeable wall 12 against a fluid outside dispenser system 10. The materials used for forming the space consuming member that are swellable and expandable are polymeric materials neat and, optionally, polymeric materials blended with osmotic agents that interact with water or biological fluid, absorb the fluid and swell or expand to an equilibrium state. The polymer exhibits the ability to retain a significant fraction of imbibed fluid in the polymer molecular structure. The polymers in a preferred embodiment are gel polymers that can swell or expand to a very high degree, usually exhibiting a 2 to 50 fold volume increase. The swellable, hydrophilic polymers, also known as osmopolymers, can be noncross-linked or lightly cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include poly(hydroxyalkylmethacrylate) having a molecular weight of from 5,000 to 5,000,000; poly(vinylpyrrolidone) having a molecular weight of from 10,000 to 360,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; water swellable copolymer produced by a dispersion of finely divided copolymer of maleic anhydride with styrene, ethylene, propylene, or isobutylene; water swellable polymer of N-vinyl lactams; and the like.

Other gelable, fluid imbibing and fluid retaining polymers useful such for forming the hydrophilic, expandable push member 20 include pectin having a molecular weight ranging from 30,000 to 300,000; polysaccharides such as agar, acacia, karaya, tragacanth, algins and guar; Carbopol ®, an acrylic acid polymer, which is a carboxyvinyl polymer, sometimes referred to as carboxypolymethylene, a polymer of acrylic acid cross-linked with a polyallyl ether of sucrose having a 275,000 to 3,250,000 molecular weight, as described in U.S. Pat. Nos. 2,798,053 and 2,909,462 and available as Carbopols ® 934, 940 and 941, and its salt derivatives; polyacrylamides; water-swellable indene maleic anhydride polymers; Good-rite ® polyacrylic acid having a molecular weight of 80,000 to 200,000; Polyox ® polyethylene oxide polymers having a molecular weight of 100,000 to 5,000,000; starch graft copolymers; Aqua-Keep ® acrylate polymers with water absorbability of about 400 times its original weight; diesters of polyglucan; a mixture of cross-linked polyvinyl alcohol and poly(N-vinyl-2-pyrrolidone); zein available as prolamine; poly(ethylene glycol) having a molecular weight of 4,000 to 100,000, and the like. In a preferred embodiment, the expandable member is formed from polymers and polymeric compositions that are thermoformable. Representative polymers possessing hydrophilic properties are known in U.S. Pat. Nos. 3,865,108; 4,002,173; 4,207,893; 4,327,725, and in *Handbook of Common Polymers*, by Scott and Roff, published by Cleveland Rubber Company, Cleveland, Ohio.

The dosage form comprising the granules can be manufactured by standard techniques. For example, one manufacture comprises blending a drug such as ibuprofen and a hydroxyalkylcellulose ether in a granule forming solvent and evaporating the solvent to form coprecipitated drug and the cellulose ether. The granule then is surrounded with a film such as polyvinylpyrrolidone. In another manufacture the process for providing the granules comprises dissolving the pharmaceutically acceptable cellulosic ether and the drug in a solvent to form a semi-dry mass by evaporating the solvent under mild conditions under vacuum. The semi-dry mass is granulated to form small uniform granules that can be made into a layer by direct compression. Alternatively, the solvent may be evaporated by spray-drying the solution. In a different method, the solvent may be evaporated and the drug added to the solution to form a paste that can be granulated to obtain small granules. The granules can be compressed into layers, comprising a homogenous blend of the polymeric cellulose ether and the drug. The granules, when surrounded by the film, are in essence miniature drug delivery systems, which exhibit osmotic properties and release the drug for delivery from the dosage form.

The granules in another embodiment are prepared by a wet granulation procedure using an organic cosolvent as a granulating fluid. The ingredients forming the granules in this manufacture are individually passed through a screen and then thoroughly blended in a mixer. Next, poly(vinylpyrrolidone) or its copolymer is dissolved in a portion of the granulation fluid, and the solution added slowly to the dry powder blend with continual mixing in a blender. The wet mass is then forced through a screen onto oven trays and dried for 18 to 24 hours. The dry granules are then pressed into a layer. In another manufacture, after the granules are dry, the granules are sprayed with a film forming solution to surround the granule with the film. After the film-coated granules are dry, they are pressed into a layer. The composition forming granules in the above manufacturing processes are tabletted using a Manesty ® tablet press. The speed of the press is set at 30 rpm and the maximum load set at 2 tons. Different dosage forms are tabletted using the press, and the dosage form can have different shapes, such as round using a 7/32 inch (5.55 mm) punch, or a 3/16 inch (4.76 mm) round, standard concave punch.

The wall of the osmotic dosage systems can be formed in one other technique using the air suspension procedure. This procedure consists in suspending and tumbling the drug compressed core forming compartment in a current of air and a wall forming solution comprising cellulose acetate and methylene chloride and methanol until the wall is applied to the drug forming compartment. The air suspension procedure is well suited for independently forming the wall. The air suspension procedure is described in U.S. Pat. No. 2,799,241; in *J. Am. Pharm. Assoc.*, Vol. 48, pp 451–459, (1959); and ibid. Vol. 49, pp 82–84, (1960). The osmotic dosage form also can be coated with the wall forming composition with a Wurster ® air suspension coater, using a methylene dichloride/methanol cosolvent 80/20 v/v, using 2.5% to 4% solids. The Aeromatic ® air suspension coater using a methylene dichloride/methanol cosolvent 87/13 v/v, also can be used for applying the wall. Other wall forming techniques such as pan coating system, wall forming composition is deposited by successive spraying of the composition on the drug, accompanied by tumbling in a rotating pan. An exit port is drilled through the semipermeable wall and the systems are dried for removing the solvent. Generally the semipermeable wall formed by these techniques will have a thickness of 2 to 20 mils, with a presently preferred thickness of 4 to 10 mils.

Exemplary solvents suitable for manufacturing the wall include inert inorganic and organic solvents that do not adversely harm the wall, the lamina and the final systems. The solvents broadly include members selected from the group consisting of alcohols, ketones, esters, ethers, aliphatic hydrocarbons, halogenated solvents, cycloaliphatic solvents, aromatic, heterocyclic, aqueous solvents and mixtures thereof.

The following examples illustrate means and methods for carrying out the present invention. The examples are merely illustrative and they should not be considered as limiting the scope of the invention, as these examples and other equivalents thereof will become more apparent to those versed in the pharmaceutical dispensing art in the light of the present disclosure, the drawings and the accompanying claims.

EXAMPLE 1

A dosage form, shaped, adapted and designed as an oral osmotic drug delivery system is made as follows: first, 369 g of pharmaceutically acceptable hydroxypropyl cellulose comprising an average molecular weight of 80,000 is passed through a 20 mesh screen, then 162 g of pharmaceutically acceptable polyvinylpyrrolidone comprising an average molecular weight of 40,000 is passed through a 40 mesh screen. Next, the two screened ingredients are blended with 66 g of ibuprofen to form a homogenous blend. The blend is suspended in a fluidized bed and sprayed with an atomized spray of ethanol:water (70:30 vol:vol) solution until homogenous granules form. These granules then are passed through a 20 mesh screen. Finally, the screened granulation is mixed with 3 g of magnesium stearate in a rollermill for 5 minutes.

Next, 389 g of pharmaceutically acceptable sodium carboxymethylcellulose having a 700,000 average molecular weight, 174 g of sodium chloride, 30 g of pharmaceutically acceptable hydroxypropyl methylcellulose having a 11,200 molecular weight and 6 g of ferric oxide are passed separately through a 40 mesh screen. Next, all the freshly screened ingredients are mixed to produce a homogenous blend. Then, 300 ml of denatured anhydrous ethanol is added slowly to the blend with further mixing over 5 minutes. The freshly prepared wet granulation is passed through a 20 mesh screen, allowed to dry at room temperature for 16 hours, and again passed through a 20 mesh screen. The screened homogenous granulation is mixed with 1.5 g magnesium stearate in a rollermill for about 5 minutes.

Next, the drug composition and the push composition are compressed into a bilaminate tablet arrangement. First, 200 mg of the drug composition is added to a 0.375 inch (9.5 mm) punch and tamped, then, 140 mg of the push composition is added to the punch and the two laminae pressed under a pressure of 2.7 tons into a contacting laminated arrangement.

Then, the bilaminate arrangements are coated with a semipermeable wall. The wall forming composition comprises 93% cellulose acetate having an acetyl content of 39.8%, and 7% polyethylene glycol having a molecular weight of 3,350. The wall forming composition is dissolved in acetone:water (90:10 wt:wt) solvent to make a 4% solid solution. The wall forming composition is sprayed onto and around the bilaminate in an Aeromatic Air Suspension Coater ®.

Finally, a 25 mil exit orifice is drilled mechanically on the drug side of the osmotic dosage form. The residual solvent is removed by drying the dosage form for 48 hours at 50° C. and 50% humidity, followed by drying the dosage form for 2 hours at 50° C. to remove any excess moisture. The dosage form delivers drug over a prolonged period of 21 hours.

EXAMPLE 2

An osmotic dosage form for delivering indomethacin is prepared as follows: first 135 g of pharmaceutically acceptable hydroxypropylcellulose exhibiting a 80,000 average molecular weight is passed through a 20 mesh screen; then, 33 g of indomethacin are passed through a 20 mesh screen and the two ingredients blended in a commercial blender for 15 minutes to produce a homogenous blend. Next, 81 g of polyvinylpyrrolidone is mixed with 3,000 ml of a cosolvent comprising ethanol:water (70:30 vol:vol) and the homogenous blend coated with a film of polyvinylpyrrolidone in a fluidized bed with an atomized spray. The film coated granules are passed through a 20 mesh screen and dried at room temperature for 18 hours to 24 hours.

The dried granulation then is mixed with 1 g magnesium stearate in a rollermill for about 5 minutes. Next, an expandable composition is prepared by passing 145 g of carboxypolymethylene possessing a molecular weight of 3,000,000 through a 40 mesh screen, followed by passing individually through the 40 mesh screen 87 g of sodium chloride, and 15 g of hydroxypropylmethylcellulose having a 11,300 molecular weight. Next, the screened ingredients are blended with 175 ml of denatured alcohol for 5 minutes. Then, the wet granulation is passed through a 20 mesh screen, dried in an oven for 16 hours at 30° C., and again passed through a 20 mesh screen. The screened granulation is mixed with 0.75 g of stearic acid in a 2-roller mill for 5 minutes.

Next, the two lamina forming compositions are compressed into a bilaminate using a Manesty ® press. First, the drug granules is added to the Manesty press and pressed to form a lamina. Then, the expandable composition is added Manesty press and pressed to form a bilaminate arrangement.

Next, the bilaminate is coated with a semipermeable wall. The semipermeable wall weighs 35.2 mg and comprises 96% cellulose acetate having a 39.8 acetyl content, 2.5% polyethylene glycol 3,350 and 2.5% hydroxypropylmethylcellulose having a number average molecular weight of 11,300. The semipermeable wall is applied in an AccelaCota ® rotating open coater. The coating solution comprising the cellulose acetate, the polyethylene glycol and the hydroxypropylmethylcellulose dissolved in methylene chloride:methanol (90:10 wt %) to give a 4% solution.

After drying, a passageway is formed in the wall using a laser generator. The dosage form delivers drug over a prolonged period of 24 hours through the passageway.

DISCLOSURE OF A METHOD OF USING THE INVENTION

An embodiment of the invention pertains to a method for delivering a therapeutic drug at a controlled rate orally to a warm-blooded animal in need of drug therapy. The method comprises the steps of: (A) admitting into the warm-blooded animal, such as a patient, a dosage form comprising: (1) a wall surrounding a compartment, the wall comprising at least in part a semipermeable polymeric composition permeable to the passage of exterior fluid and substantially impermeable to the passage of drug; (2) a layer in the compartment comprising a granule drug formulation comprising a dosage unit amount of an orally administrable drug for performing a therapeutic program; (3) a layer in the compartment comprising granules of an expandable composition for imbibing and absorbing fluid for pushing and displacing the drug from the dosage form; and (4) at least one passageway in the wall for releasing the drug; (B) imbibing fluid through the semipermeable part of the wall at a rate determined by the permeability of the semipermeable wall and the osmotic pressure gradient across the semipermeable wall causing the osmotic layer to expand and swell; and (C) delivering the beneficial drug from the dosage form through the exit passageway to the warm blooded animal over a prolonged period of time.

In summary, it will be appreciated that the present invention contributes to the art and unobvious dosage form that possesses practiced utility, can administer a drug at a dose metered release rate per unit time. While the invention has been described and pointed out in detail with reference to operative embodiments thereof, it will be understood that those skilled in the art that various changes, modifications, substitutions and omissions can be without departing from the spirit of the invention. It is intended, therefore, that the invention embraces those equivalents within the scope of the claims which follow.

We claim:

1. A dosage form for administering a drug to a warm-blooded animal, wherein the dosage form comprises:
    (a) a wall that surrounds;
    (b) a compartment;
    (c) a layer in the compartment comprising granules, the granules comprising a film comprising a polyvinylpyrrolidone polymer comprising a 10,000 to 500,000 molecular weight, that surrounds a drug possessing a solubility of 1 part of drug in less than 1 part of aqueous solvent to 1 part of drug in more than 10,000 parts of aqueous solvent, and a hydroxyalkylcellulose comprising a 10,000 to 1,000,000 molecular weight;
    (d) a layer in the compartment comprising a composition that imbibes fluid, consumes space and displaces the drug from the dosage form; and
    (e) at least one exit passageway in the wall that connects the exterior with the interior of the dosage form for delivering the drug to the warm-blooded animal over a prolonged period of time.

2. The dosage form for administering the drug to a warm-blooded animal according to claim 1, wherein the hydroxyalkylcellulose is a member selected from the group consisting of hydroxymethylcellulose, hydroxyethylcellulose, hydroxypropylcellulose, hydroxybutylcellulose, hydroxypentylcellulose, hydroxytertpentylcellulose, hydroxyhexylcellulose and hydroxyisohexylcellulose.

3. A dosage form for administering a drug to a warm-blooded animal, wherein the dosage form comprises:
    (a) a wall that surrounds;
    (b) a compartment;
    (c) a layer in the compartment comprising granules, the granules comprising a polyvinylpyrrolidone copolymer film that surrounds a hydroxyalkylcellulose comprising a 10,000 to 1,000,000 molecular weight, and a drug solute possessing a solubility of 1 part of drug solute in less than 1 part of aqueous solvent to 1 part of solute in more than 10,000 parts of aqueous solvent;
    (d) a layer in the compartment comprising a formulation that imbibes fluid, consumes space and thereby displaces the drug from the dosage form; and
    (e) at least one passageway in the wall that connects the exterior with the interior of the dosage form for delivering the drug to the warm-blooded animal over a prolonged period of time.

4. A Method for administering a drug to a patient, wherein the method comprises:
    (a) admitting into the patient a dosage form comprising:
        (1) a wall comprising at least on part a composition permeable to the passage of fluid, which wall surrounds;
        (2) a compartment;
        (3) a layer in the compartment comprising granules, the granules comprising a film comprising a member selected from the group consisting of polyvinylpyrrolidone and a polyvinylpyrrolidone copolymer, which film surrounds from 0.01 weight percent to 80 weight percent of a drug possessing a solubility of 1 pat of drug in less than 1 part of aqueous solvent to 1 part of drug in more than 10,000 parts of aqueous solvent, said drug a member selected from the group consisting of Drugs that act on peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, organ systems, reproductive systems, autocoid systems, alimentary and excretory systems, and a hydroxyalkylcellulose comprising a 10,000 to 1,000,000 weight;

(4) a layer in the compartment comprising a composition that imbibes fluid, consumes space and displaces the drug from the dosage form; and
(5) at least one passageway in the wall that connects the exterior with the interior of the dosage form for delivering the drug from the dosage form;

(b) imbibing fluid into the dosage form for contacting the layer that displaces the drug; thereby, (c) administering the drug to the patient in a therapeutically effective amount over time.

5. A method for administering a drug to a warm-blooded animal according to claim 4, wherein the polyvinylpyrrolidone copolymer is a member selected from the group consisting of polyvinylpyrrolidone vinyl acetate copolymer, polyvinylpyrrolidone vinyl alcohol copolymer, polyvinylpyrrolidone vinyl chloride copolymer, polyvinylpyrrolidone vinyl fluoride copolymer, polyvinylpyrrolidone vinyl butyrate copolymer, polyvinylpyrrolidone vinyl laurate copolymer, and polyvinylpyrrolidone vinyl stearate copolymer.

6. A method for administering a drug to a warm-blooded animal according to claim 4, wherein the hydroxyalkylcellulose comprises a member selected from the group consisting of hydroxymethylcellulose, hydroxyethylcellulose, hydroxypropylcellulose, hydroxybutylcellulose, hydroxypentylcellulose, hydroxytertpentylcellulose, hydroxyhexylcellulose and hydroxyisohexylcellulose.

* * * * *

UNITED STATES PATENT AND TRADEMARK OFFICE
CERTIFICATE OF CORRECTION

PATENT NO. : 5,035,897

DATED : July 30, 1991

INVENTOR(S) : AYER, Atul; KUCZYNSKI, Anthony L.; WONG, Patrick S.

It is certified that error appears in the above-identified patent and that said Letters Patent is hereby corrected as shown below:

In claim 4, column 14, line 40, "Method" should read ----method----.

In claim 4, column 14, line 44, "on" should read ----in----.

In claim 4, column 14, line 54, "pat" should read ----part----.

Signed and Sealed this

Second Day of March, 1993

*Attest:*

STEPHEN G. KUNIN

*Attesting Officer*    *Acting Commissioner of Patents and Trademarks*